US010588665B2

(12) United States Patent
Marcus

(10) Patent No.: US 10,588,665 B2
(45) Date of Patent: *Mar. 17, 2020

(54) INTERMAXILLARY FIXATION DEVICE AND METHOD OF USING SAME

(71) Applicant: Jeffrey R. Marcus, Chapel Hill, NC (US)

(72) Inventor: Jeffrey R. Marcus, Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/996,728

(22) Filed: Jun. 4, 2018

(65) Prior Publication Data

US 2018/0271560 A1 Sep. 27, 2018

Related U.S. Application Data

(63) Continuation of application No. 12/329,306, filed on Dec. 5, 2008, now Pat. No. 10,010,347.

(60) Provisional application No. 61/017,861, filed on Dec. 31, 2007.

(51) Int. Cl.
*A61B 17/64* (2006.01)
(52) U.S. Cl.
CPC .................. *A61B 17/6433* (2013.01)
(58) Field of Classification Search
CPC ............ A61B 17/6433; A61B 17/8071; A61B 17/7811; A61C 7/00; A61C 7/282; A61C 7/36; A61F 2/2803; A61F 2/3099
USPC ........... 433/3, 6, 9, 18, 19, 20, 24, 173, 215
See application file for complete search history.

(56) References Cited

U.S. PATENT DOCUMENTS

| 49,779 | A | | 9/1865 | Montignani |
| 83,195 | A | | 10/1868 | Middleton |
| 592,250 | A | | 10/1897 | Kuenzle et al. |
| 1,638,006 | A | | 8/1927 | Aderer |
| 2,481,177 | A | | 9/1949 | Tofflemire |
| 2,502,902 | A | * | 4/1950 | Tofflemire ........... A61F 5/05891 433/23 |
| 2,580,821 | A | | 1/1952 | Nicola |

(Continued)

FOREIGN PATENT DOCUMENTS

| DE | 29615779 U1 | 1/1997 |
| DE | 19826860 A1 | 4/1999 |

(Continued)

OTHER PUBLICATIONS

Extended European Search Report for EP17001891 dated Apr. 5, 2018.

(Continued)

*Primary Examiner* — Yogesh P Patel
(74) *Attorney, Agent, or Firm* — Lerner, David, Littenberg, Krumholz & Mentlik, LLP

(57) ABSTRACT

A medical apparatus having a bar, the bar having a slot extending laterally along the bar; and a plurality of hooks, wherein the bar is an arch bar that is configured to be attached to a mandible or a maxilla. Such medical apparatuses may also have a plurality of arch bar fasteners, wherein each arch bar fastener is a bone screw having a threaded shaft and a compound head, the compound head having a threaded bore configured to receive a set screw. The medical apparatus may be used in methods to fixate a maxillary or mandibulary arch, or to aid in reducing a fracture of the mandible or maxilla.

11 Claims, 6 Drawing Sheets

(56) References Cited

U.S. PATENT DOCUMENTS

| | | | |
|---|---|---|---|
| 2,805,777 | A * | 9/1957 | Larson ............... B25H 3/04 |
| | | | 211/70.1 |
| 3,474,779 | A | 10/1969 | Wall |
| 4,108,313 | A * | 8/1978 | Bogar, Jr. ........... A47B 81/005 |
| | | | 211/106.01 |
| 4,202,328 | A | 5/1980 | Sukkarie |
| 4,230,104 | A | 10/1980 | Richter |
| 4,372,450 | A * | 2/1983 | Licari ............... A47G 25/0678 |
| | | | 211/106.01 |
| 4,639,219 | A | 1/1987 | Gagin |
| 4,797,095 | A | 1/1989 | Armstrong et al. |
| 4,904,188 | A | 2/1990 | Baurmash |
| 5,087,202 | A | 2/1992 | Krenkel |
| 5,137,158 | A | 8/1992 | Brockway |
| 5,839,899 | A | 11/1998 | Robinson |
| 5,842,856 | A | 12/1998 | Casey |
| 5,853,092 | A | 12/1998 | Goodman et al. |
| 6,053,919 | A | 4/2000 | Talos et al. |
| 6,086,365 | A | 7/2000 | Fields |
| 6,227,861 | B1 | 5/2001 | Cartledge et al. |
| 6,257,884 | B1 | 7/2001 | Chang |
| 6,595,774 | B1 | 7/2003 | Risse |
| 6,669,697 | B1 | 12/2003 | Pisharodi |
| 6,827,574 | B2 | 12/2004 | Payton |
| 6,896,514 | B2 | 5/2005 | DeVincenzo |
| D533,745 | S * | 12/2006 | Rodrigue ............... D6/566 |
| 7,322,987 | B2 | 1/2008 | Schendel |
| 7,351,058 | B2 | 4/2008 | Fore et al. |
| 8,282,635 | B1 | 10/2012 | Amato |
| 8,662,889 | B2 | 3/2014 | Baker |
| 8,979,529 | B2 | 3/2015 | Marcus |
| 2001/0018176 | A1 | 8/2001 | Branemark |
| 2002/0013586 | A1 | 1/2002 | Justis et al. |
| 2002/0143336 | A1 | 10/2002 | Hearn |
| 2002/0150856 | A1 | 10/2002 | Payton |
| 2003/0160552 | A1 | 8/2003 | Bacho et al. |
| 2004/0086824 | A1 | 5/2004 | Kesling |
| 2004/0102775 | A1 * | 5/2004 | Huebner ............... A61B 17/80 |
| | | | 606/86 B |
| 2004/0152046 | A1 | 8/2004 | Minoretti et al. |
| 2005/0059971 | A1 | 3/2005 | Michelson |
| 2005/0090825 | A1 * | 4/2005 | Pfefferle ............ A61B 17/8085 |
| | | | 606/283 |
| 2005/0261690 | A1 | 11/2005 | Binder et al. |
| 2005/0282115 | A1 | 12/2005 | Gedebou |
| 2006/0069389 | A1 | 3/2006 | Knopfle |
| 2006/0078849 | A1 | 4/2006 | Parks |
| 2007/0190475 | A1 | 8/2007 | Fore et al. |
| 2007/0254259 | A1 | 11/2007 | DeVincenzo et al. |
| 2007/0259306 | A1 | 11/2007 | Raines et al. |
| 2008/0050691 | A1 | 2/2008 | Baughman et al. |
| 2008/0081315 | A1 | 4/2008 | Kim et al. |
| 2009/0036889 | A1 | 2/2009 | Callender |
| 2011/0152946 | A1 | 6/2011 | Frigg et al. |
| 2011/0152951 | A1 | 6/2011 | Baker |

FOREIGN PATENT DOCUMENTS

| | | |
|---|---|---|
| DE | 19859503 A1 | 7/2000 |
| EP | 1468656 B1 | 10/2005 |
| EP | 1385435 B1 | 12/2006 |
| FR | 2760631 A1 | 9/1998 |
| GB | 1231425 A | 5/1971 |
| JP | H111164843 A | 6/1999 |
| WO | 9727815 A1 | 8/1997 |
| WO | 9915115 A1 | 4/1999 |
| WO | 2007095577 A2 | 8/2007 |
| WO | 2010025263 A1 | 3/2010 |
| WO | 2011063368 A1 | 5/2011 |

OTHER PUBLICATIONS

Extended European Search Report issued on European Application 08859747.1, dated Mar. 16, 2015. (091034-0115).

International Search Report and Written Opinion for PCT/US2008/085680 dated Jan. 29, 2009.

International Search Report and Written Opinion for PCT/US2008/085685 dated Feb. 6, 2009.

Supplementary European Search Report for Application No. EP 08868823, dated Jul. 22, 2013, 5 pages.

Communication issued on European Application 08859747.1, dated Mar. 11, 2016 (091034-0115).

* cited by examiner

INTERMAXILLARY FIXATION DEVICE AND METHOD OF USING SAME

CROSS-REFERENCE TO RELATED APPLICATIONS

This application is a continuation of U.S. application Ser. No. 12/329,306, filed on Dec. 5, 2008, and claims the benefit of U.S. Provisional Patent Application No. 61/017,861, filed Dec. 31, 2007 the disclosures of which are incorporated herein by reference

BACKGROUND OF THE INVENTION

The invention is generally related to maxillofacial/dental devices. More specifically, the invention is related to devices for maxillary and/or mandibular fixation and/or stabilization.

The fixation or stabilization of the upper and lower dental occlusal arches to one another is known as intermaxillary fixation (IMF), also known as maxillo-mandibular fixation (MMF). IMF has historically been a necessity in the treatment of all reconstructive jaw procedures.

The earliest methods for providing IMF consisted of wiring techniques, in which metallic wires were placed around one or more (adjacent) teeth at their base(s) and were then twisted down to the teeth in a secure manner. When a wire is passed around a tooth (or teeth) at the base in such a way, it may be termed a circumdental wire ligature (CWL). Multiple CWL's can be placed along the span of the dental arch in a series, or the wire may also be fashioned such that a single continuous strand incorporates multiple teeth along the arch securely. In whatever manner this is accomplished, both upper and lower arches are so treated, and subsequently the jaws are then secured to one another with wire loops or elastics incorporating single or multiple CWLs on the opposing jaws, thus accomplishing IMF.

Arch bars (or arch wires) are known to those of skill in the art. Arch bars involve the use of a linear metal bar or wire that may be applied and secured to the dental arch form. Arch bars typically have a plurality of hooks/tabs facing in a single direction. The arch bars and their corresponding hooks are placed in opposing directions for the upper and lower jaws so that wire loops or elastics could securely affix the jaws together. Arch bars typically impart stability to one or both the maxillary or mandibular arch. The relatively rigid bar spanning along the dental arch provides stability along the upper border of either jaw even when a fracture is present between teeth. A plurality of hooks allows placement of elastics or wire loops between the jaws at varying angles to potentially affect varying, advantageous tension vectors. The two common methods of securing all arch bars are (1) via CWL placed around the teeth in routine fashion but incorporating the arch bar; and (2) via orthodontic adhesives of a variety of types.

However, both methods suffer drawbacks. For example, the most common means to secure arch bars is via multiple circumdental wire ligatures. This is a time-consuming process, associated with significant discomfort and potential for dental injury. The wire ligatures themselves are uncomfortable and often must be adjusted/tightened by the treating physician. Removal of arch bars applied using CWL's, is equally uncomfortable, and there is further potential for dental injury. In addition, in some CWL's require removal under operative anesthesia, with the associated risks of anesthesia.

While orthodontic adhesives are known, they too have disadvantages, in large part due to the conditions under which IMF is performed. For example, IMF is often performed by a surgical specialist, who is unfamiliar with the techniques and procedures used by orthodontists and dentists in the area of dental adhesives. The procedures are also, many times, conducted in a trauma setting where damage and blood loss limit the ability to work with such adhesives—which require a relatively clean, dry field for efficacy.

Adhesive techniques and circumdental wiring techniques both require adequate dentition. Both techniques may be severely limited or even precluded in conditions for dental injury, loss, or preexisting poor dental health.

Another method of IMF utilizes individual screws, placed in the bone between tooth roots, with a portion of the screw projecting external to the gingival or mucosa. Two or more IMF screws are typically placed into each of the upper and lower jaws. A wire loop is then either wrapped around the exposed portion of two opposing screws, or through a hole that is drilled through each of the two opposing screw heads, to provide IMF.

The advantages of IMF screw fixation include speed of placement and comfort. The screws rarely require adjustment, are well-tolerated, and are easily removed. However, IMF screws do not provide stability along the dental arch as does an arch bar. Ideally, IMF is used not only for immobilization, but also for accurate restoration of occlusion. For fractures occurring between teeth, IMF screws do not provide upper border stabilization nor flexible technical application methods to optimize occlusion. Finally, it is difficult (if not impossible) to apply elastics between IMF screws. Elastic IMF is safer than wiring the jaws together, and is often preferred for specific fracture types in which the surgeon would prefer the patient to have guided mobility of the jaws rather than relative immobilization.

Most of the technologies proposed for IMF technologies to date have been developed by orthodontists and oral surgeons. These dental specialists have been understandably inclined to consider only methods which involve fixation to teeth, a concept that has been historically accepted and perpetuated since the early 1900's. The most significant developments in reconstructive jaw surgery in the modern era have focused largely on methods for internal fixation (plating), rather than IMF. However, internal fixation is not a replacement for IMF, nor does is preclude the need for IMF in most cases, which is still a mandatory procedure for reconstruction of the dental arches.

Despite early developments in dental arch fixation technology, and advanced developments in other dental areas, there is currently no way to anchor existing arch bars to bone or other prosthetic dental devices using existing technologies.

BRIEF SUMMARY OF THE INVENTION

In one aspect, a medical apparatus is provided comprising a bar comprising: a slot extending laterally along the bar; and a plurality of hooks; wherein the bar is an arch bar that is configured to be attached to a mandible or a maxilla. In some embodiments, the medical apparatus further comprises a plurality of arch bar fasteners, wherein each arch bar fastener comprises a bone screw comprising a threaded shaft and a compound head, the compound head comprising a threaded bore configured to receive a set screw. In such embodiments, the set screw comprises a threaded shaft, a head, and a seating face, wherein the seating face comprises a roughened surface.

In some embodiments, the bar further comprises a roughened area on a face of the bar, adjacent to the slot, and configured to engage a set screw comprising a threaded shaft, a head, and a seating face, wherein the seating face comprises a roughened surface. In yet other embodiments, the slot is segmented by a plurality of lateral supports to form a plurality of slots. In yet further embodiments, the hooks are capable of receiving a wire or an elastic material, or other flexible, rigid, or semi-rigid material. In some embodiments, the bar is a bendable bar.

In another aspect, a method is provided comprising, stabilizing a mandibular arch or a maxillary arch using an arch bar. In some embodiments, such methods further comprise bending the arch bar to approximate the mandibulary arch or the maxillary arch; securing plurality of arch bar fasteners into the mandible or the maxilla, the arch bar fasteners comprising a threaded post and a compound head, the compound head comprising a threaded bore; inserting a plurality of set screws through the slot at positions corresponding to the placement of the arch bar fasteners; and screwing the plurality of set screws into the threaded bores.

In another aspect, a method of reducing a fracture in a mandible or maxilla is provided, comprising: bending an arch bar to approximate the mandibulary arch or the maxillary arch; securing a plurality of arch bar fasteners into the mandible or the maxilla around the fracture, the arch bar fasteners comprising a threaded post and a compound head, the compound head comprising a threaded bore; inserting a plurality of set screws through the slot at positions corresponding to the placement of the arch bar fasteners; screwing the plurality of set screws into the threaded bores without tightening the set screw to the bar; reducing the fracture; and tightening the plurality of set screws.

In another aspect, a medical apparatus is provided comprising: a first arch bar; and a second arch bar, wherein, the first arch bar is configured to be attached to a subject's maxilla with a plurality of arch bar fasteners; the second arch bar is configured to be attached to a subject's mandible with a plurality of arch bar fasteners; and the first arch bar is attached to the second arch bar via a wire, an elastic, or other flexible, rigid, or semi-rigid material.

In another aspect, a method is provided comprising using the medical apparatus comprising: a first arch bar; and a second arch bar, wherein, the first arch bar is configured to be attached to a subject's maxilla with a plurality of arch bar fasteners; the second arch bar is configured to be attached to a subject's mandible with a plurality of arch bar fasteners; and the first arch bar is attached to the second arch bar via a wire, an elastic, or other flexible, rigid, or semi-rigid material, to fixate a mandibulary arch and a maxillary arch. In some embodiments, the method is capable of restoring or creating dental occlusion between existing native dentition, dental implants, or other dental appliances.

In some embodiments, the method further comprises bending the first arch bar to approximate the maxillary arch; bending the second arch bar to approximate the mandibulary arch; securing the first arch bar to the maxillary, a prosthedontic device, or a bone graft; and securing the second arch bar to the mandible, a prosthedontic device, or a bone graft. In some such embodiments, the method further comprises applying a fastener to the hooks of the first arch bar and to the hooks of the second arch bar to enact intermaxillary fixation, and/or establish dental occlusion. In other such embodiments, the fastener is a wire, an elastic, or other flexible, or semi-rigid material.

DETAILED DESCRIPTION

Arch bars are medical apparatuses for providing stabilization and/or fixation of the mandible or the maxilla, or between the mandible and maxilla. Such medical apparatuses may be used for a number of medical needs such as, but not limited to, treatment of fracture, restoration and fixation of dental occlusion, and maxillary and/or mandibular reconstruction with or without bone grafts. The arch bars may be affixed to bone or prosthedontic devices, thus precluding the need for CWLs, or the use of adhesives.

Figure 1:
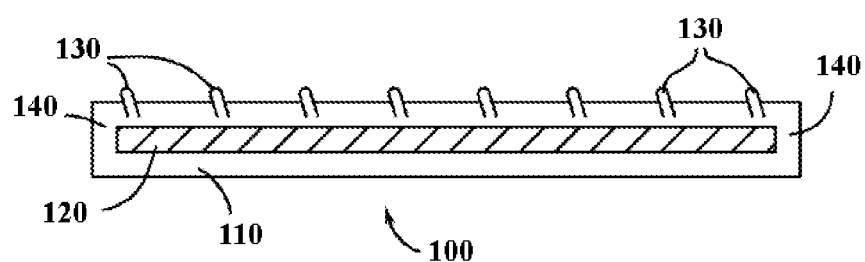
FIG. 1 is a frontal view of an arch bar according to one embodiment of the invention.

As shown in FIG. 1, an arch bar 100 is a bar 110 having a slot 120, and a plurality of hooks 130. The slot 120 is defined by lateral supports 140 of the bar 110. Such lateral supports 140 provide rigidity to the bar 110 around the slot 120. The slot 120 is configured to receive a setting fixture, or a plurality of setting fixtures for securing the arch bar 100 to bone such a mandible or maxilla, or to a prosthedontic apparatus.

Figure 2:
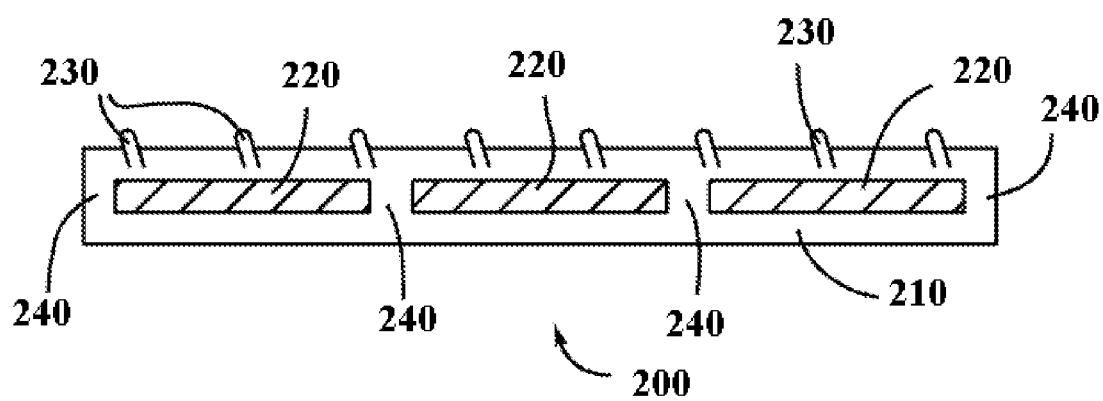
FIG. 2 is a frontal view of an arch bar according to one embodiment of the invention.

As shown in FIG. 2, and according to one embodiment, an arch bar 200 is a bar 210 having a plurality of slots 220, and a plurality of hooks 230. The plurality of slots 220 may be two slots, three slots as shown in FIG. 2, four slots, five slots, or more. The application desired will determine the number of slots provided in the arch bar 220. The slots 220 are defined by a plurality of lateral supports 240. Such lateral supports 240 provide rigidity to the bar 210 around the slots 220. The slots 220 are configured to receive a plurality of setting fixtures for securing the arch bar 100 to bone such a mandible or maxilla, or to a prosthedontic apparatus.

Figure 3:
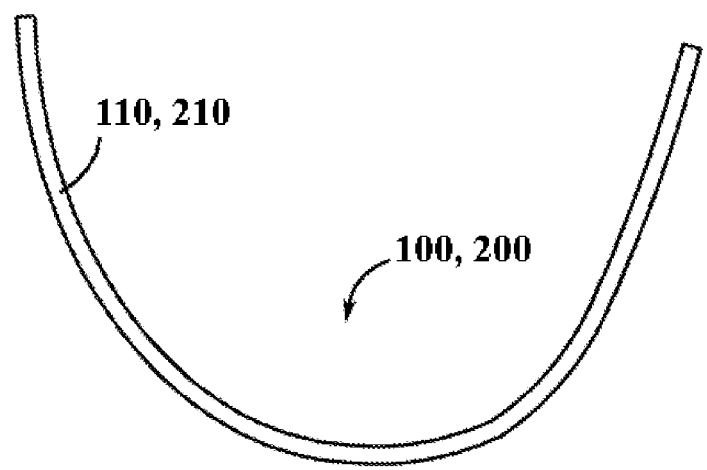
FIG. 3 is a top view of an arch bar bent to approximate a mandibulary or maxillary arch, according to one embodiment.

The bars may be either bendable or not bendable. Bending can facilitate the surgeon or medical professional's ability to approximate a maxillary or mandibular arch, as shown in FIG. 3. As used herein, the term "bendable" is to mean that the item to which the term refers, may be moved or shaped, in response to the application of an external force. Further, once moved or bent, the item does not return to its previous position, without being acted upon by a second external force. In other words, the item is bent and stays bent, until bent into another shape or position.

The arch bars may also not be bendable, instead being preformed to a rigid arch position upon manufacture, then resist bending to a new position, or which would then return to the preformed position upon attempted bending. As used herein, the term "rigid" is used to refer to an item that resists bending to a moderate force, but may be bent under extreme force as compared to a bendable item.

Figure 4:
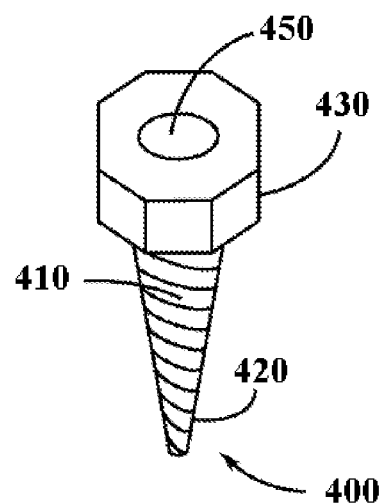
FIG. 4 is a perspective view of an arch bar fastener, according to one embodiment.
Figure 5:
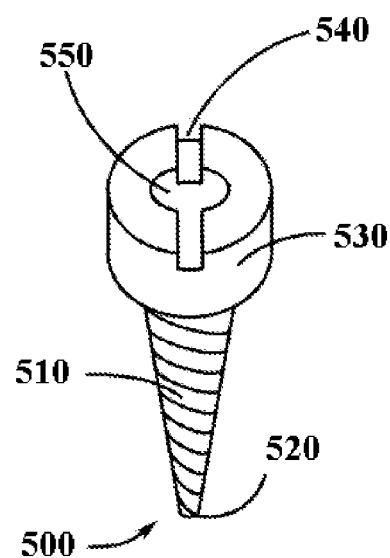
FIG. 5 is a perspective view of an arch bar fastener, according to one embodiment.

The slots 120, 220 provide a means in which to attach the bar 110, 210 to a maxilla, a mandible, or a prosthetic appliance using an arch bar fastener. FIGS. 4 and 5 show two such arch bar fasteners, 400, 500. In each of FIGS. 4 and 5, the arch bar fastener 400, 450 is a bone screw having a threaded shaft 410, 460, a tip 420, 470 and a head 430, 480. The bone screws may be inserted into a bone such as a maxilla or mandible via a pilot hole that was previously drilled, or the bone screws self-drilling or self-tapping.

The head of the arch bar fastener 400, 500 is a compound head. As used herein, "compound head," refers to a screw head having a variety of functions. As shown in FIG. 4, the head 430 may be a shaped head such as a hexhead for using a driving tool to turn the arch bar fastener into bone. The hexhead shown in FIG. 4 is for illustration only, as the shape of the head 430, 530 could be of any shape known to those of skill in the art for engaging a driver for the screw. For example, the head could be oval, triangular, square, pentagonal, or other such shape as are known to those of skill in the art. Alternatively, as shown in FIG. 5, the head 530 may have a slotted drive mechanism 540 for engaging a slotted screwdriver to drive the arch bar fastener 500 into bone. Again, the slotted drive mechanism 540 is shown only as an example, as the alternative drive mechanism may be able to be engaged by a Phillips driver, a star driver, an Allen wrench, or other driver or wrench known to those of skill in the art.

Figure 6A:
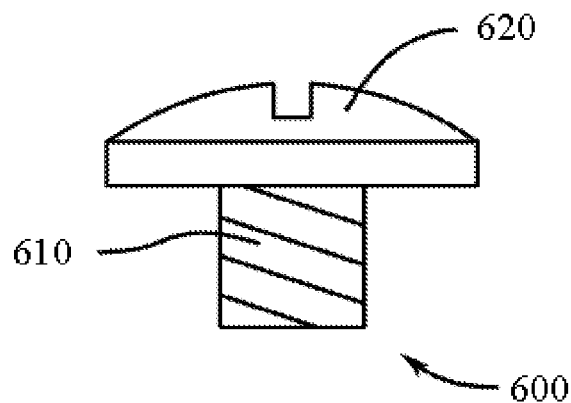
FIGS. 6A and 6B are two perspective views of a set screw, according to one embodiment.
Figure 6B:
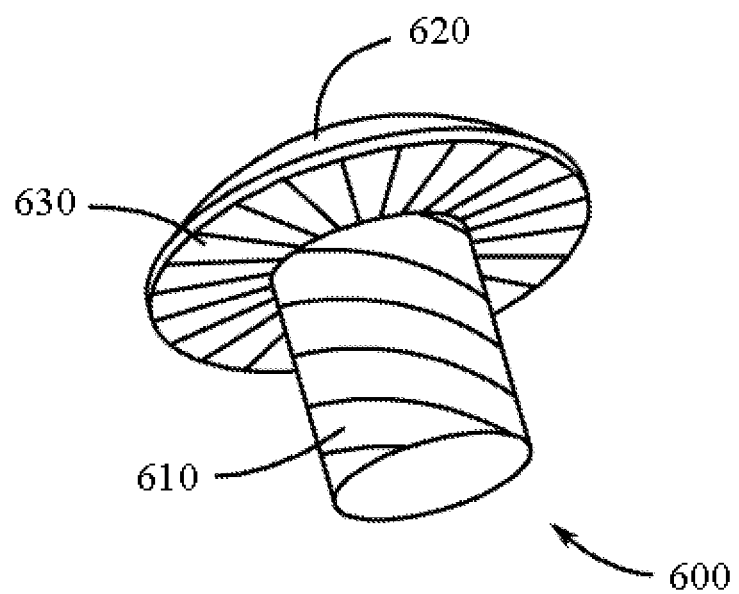

The compound head 400, 500 is also configured to receive a secondary fastener that may be inserted through the slot 120, 220 in the arch bar 100, 200 to secure the arch bar 100, 200 to the arch bar fastener 400, 500, once the arch bar fastener 400, 500 has been engaged in a bone or prosthedontic apparatus. In some embodiments, the secondary fastener is a set screw 600 as shown in FIG. 6. As such, the compound head 400, 500 may have a threaded bore 450, 550 to receive such a set screw 600. In other embodiments, the secondary fastener may be a rivet, nail, bayonet-style fastener, or other fastener known to those of skill in the art. In such embodiments, the compound head 400, 500 has a bore to receive such a rivet or nail, a complementary bayonet-style receiver to receive the bayonet-style fastener, or other receiver known to those of skill in the art.

The set screw 600, as described in some embodiments, has a threaded shaft 610, a head 620, and a seating face 630. The head 620 has a drive mechanism known to those of skill in the art and may include, but is not limited to, a slot drive, a Phillips drive, a hexhead for driving by a ratchet driver, an Allen head drive, or a star drive. The seating face 630 of the head 620 may have a roughened surface to prevent, or at least reduce, unintended "turn-out" of the set screw 600 from the arch bar fastener 400, 500. Likewise, an area around the slot 120, 220, on an outer face of the bar 110, 210 may also be roughened to complement the roughened surface of the seating face 630 of the set screw 600, and provide additional resistance to "turn-out" of the set screw.

As noted above, a plurality of hooks 130, 230 are attached to the bar 110, 210. As used herein, plurality may mean one, but typically means more than one, such as two, three, four, five, six, seven, eight, nine, ten, eleven, twelve, thirteen, fourteen, fifteen, sixteen, seventeen, eighteen, nineteen, or twenty. The hooks 130, 220 on the arch bar 100, 200 are used to attach a wire, an elastic such as a rubber band, or other device known to those of skill in the art, to the bar 110, 210 to immobilize, stabilize, or fixate the maxilla to the mandible, thus allowing for healing of the respective bones.

The hooks 130, 230 may be integrally formed with the bar 110, 210 such that they are all formed at the same time and of the same material. Alternatively, the hooks 130, 230 are threaded on one end and threaded apertures or depressions, capable of receiving the hooks are included in the bar 110, 210.

The hooks 130, 230 may be positioned on the arch bar 100 such that the opening of the hook is toward an edge of the bar 110, 210, or toward the slots 120, 220 in the bar. The size, shape, and configuration of the hooks may vary according to design preferences. The only limiting feature of the size, shape, and configuration of the hooks 130, 230 is that they must have the ability to satisfactorily allow placement of wire, elastic, or other fasteners to the arch bar 100, 200.

The arch bars, hooks, and assorted fasteners may be made from any of a variety of materials known to those of skill in the art. For example, they may be fabricated from stainless steel, titanium, other metals; acrylics; and/or other polymers.

Figure 7:
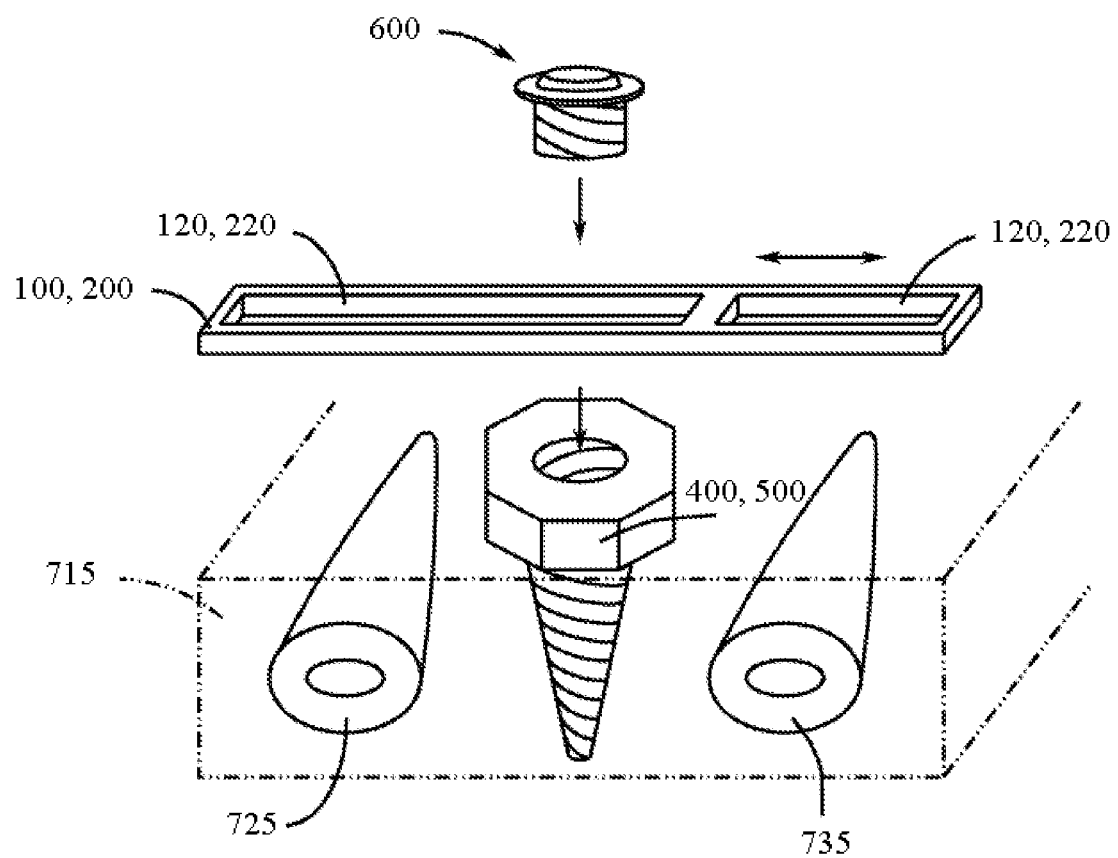
FIG. 7 is a perspective view of the attachment of an arch bar to a maxilla or mandible using an arch bar fastener and set screw, according to one embodiment.

To secure the arch bar to the maxilla or the mandible, insertion of the arch bar fasteners 400, 500 into a root should be avoided. In fact, it is desired that the arch bar fasteners 400, 500 are inserted into the bone at positions between the roots of adjacent teeth. FIG. 7 shows a perspective view of an arch bar fastener 400, 500 in place in a maxilla or mandible 715 and between the roots 725, 735 of the teeth. The slots 120, 220 then allow for placement and movement of the bar 110, 210 to the desired position prior to fixing the arch bar 100, 200 in place via the set screw 600.

Figure 8:
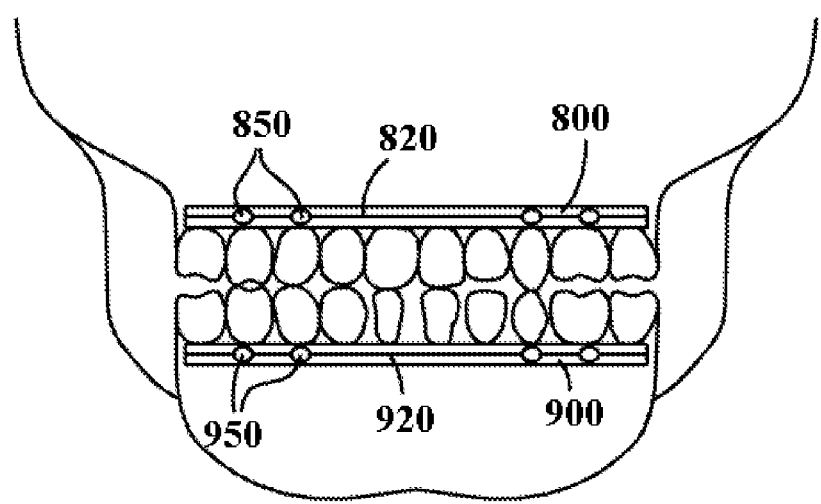
FIG. 8 is a panorex view of a dental arch with two arch bars, according to one embodiment.

In some aspects, a medical apparatus has two arch bars, as shown in FIG. 8. A first arch bar 800 is attached to the maxilla and a second arch bar 900 is attached to a mandible. The arch bars 800, 900 are attached in the same manner as above, i.e. with set screws 850, 950 through the slots 820, 920. The hooks on each of the arch bars 800, 900 are opposed to one another so that the securing wires, elastics such as rubber bands, or other attachment devices can be hooked to the arch bars 800, 900. The securing wires or other attachment devices may be separate entities, or a single wire may be intricately woven to attach the first arch bar 800 to the second arch bar 900, thus fixating the maxilla to the mandible.

In another aspect, methods are provided for stabilizing a mandibular arch or a maxillary arch using the medical apparatuses described above. For example, the arch bar may be bent to approximate the mandibular arch or the maxillary arch of a patient in need of stabilization or fixation of the mandibular and/or maxillary arch. Arch bar fasteners are secured into the mandible, maxilla, or a prosthedontic device. Either the bending of the arch bar or the securing of the arch bar fasteners may occur first in the sequence, however, the slots in the arch bar may be used to aid in the proper positioning of the arch bar fasteners. For example, the arch bar fasteners should approximately lie in a single plane as the slots in a bent arch bar will approximate a single plane.

In another aspect, the arch bars may be used in a method for reducing a fracture of the mandible or maxilla. In the method, arch bar fasteners are inserted into a fractured mandible or maxilla. In some embodiments, the fracture has either been reduced or partially reduced to reform the natural mandibulary arch or maxillary arch. An arch bar is then set in place over the arch bar fasteners and set screws are set in place such that the arch bar is able to move along the set screws via the slots. Once the surgeon, dentist, or other medical professional fully reduces the fracture, or approves of the reduced fracture, the set screws are tightened. The arch bar is then capable of maintaining the positioning of the reduced fracture. Once set in place, the arch bar keeps the fracture reduced for healing.

In other embodiments, where both a mandibular and a maxillary arch bar are used, the methods also include securing a wire, an elastic, or other flexible or semi-rigid material between the hooks of the mandibular arch bar and the hooks of the maxillary arch bar. This may be done to establish intermaxillary fixation or dental occlusion. Such methods are known as wiring the jaws shut or intermaxillary fixation.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Additionally the phrase "consisting essentially of" will be understood to include those elements specifically recited and those additional elements that do not materially affect the basic and novel characteristics of the claimed invention. The phrase "consisting of" excludes any element not specifically specified.

The above described apparatuses and methods are used to restore, fixate, or create anew dental occlusion between existing native dentition, dental implants, or other dental appliances, or for the treatment of fracture and/or reconstructing maxillary and/or mandibular reconstruction.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, it should be understood that changes and modifications can be made therein in accordance with ordinary skill in the art without departing from the invention in its broader aspects as defined in the following claims.

The invention claimed is:

1. A medical apparatus comprising:
   a first curved arch bar configured to be placed on a mandible, the first arch bar including a first longitudinal axis, a plurality of elongated first slots extending laterally along the first longitudinal axis and defined by a plurality of first lateral supports and a plurality of integrally formed first hooks, each of the first hooks being free of holes;
   a second curved arch bar configured to be placed on a maxilla, the second arch bar including a second longitudinal axis, a plurality of elongated second slots extending laterally along the second longitudinal axis and defined by a plurality of second lateral supports and a plurality of integrally formed second hooks, each of the second hooks being free of holes;
   a plurality of first bone screws each including a first threaded shaft, the first bone screws extending through the first slots such that the first threaded shafts extend into the mandible; and
   a plurality of second bone screws each including a second threaded shaft, the second bone screws extending through the second slots such that the second threaded shafts extend into the maxilla.

2. The medical apparatus of claim 1, further comprising a wire connecting at least one of the first hooks to at least one of the second hooks, after implantation of the first and second arch bars.

3. The medical apparatus of claim 2, further comprising a plurality of wires connecting the first hooks to the second hooks.

4. The medical apparatus of claim 1, wherein the first and second arch bars are bendable.

5. The medical apparatus of claim 1, wherein each bone screw further includes a head having a width wider than a width of each slot.

6. The medical apparatus of claim 5, wherein the heads each include a slotted drive mechanism.

7. A medical apparatus comprising:
   a first curved arch bar configured to be placed on a mandible, the first arch bar including a first longitudinal axis, two elongated first slots laterally extending along the first longitudinal axis and defined by a plurality of first lateral supports and two integrally formed first hooks each being free of holes;
   a second curved arch bar configured to be placed on a maxilla, the second arch bar including a second longitudinal axis, two elongated second slots laterally extending along the second longitudinal axis and defined by a plurality of second lateral supports and two integrally formed second hooks being free of holes;
   two first bone screws configured to extend through a different of the first slots and into the mandible;
   two second bone screws configured to extend through a different of the second slots and into the maxilla;
   a first wire connecting one of the first hooks to one of the second hooks; and
   a second wire connecting another of the first hooks to another of the second hooks.

8. The medical apparatus of claim 7, wherein the bone screws include threaded shafts configured to extend into one of the mandible or maxilla.

9. The medical apparatus of claim 8, wherein the bone screws further include a head having a width wider than a width of each slot.

10. The medical apparatus of claim 9, wherein the heads include a slotted drive mechanism.

11. The medical apparatus of claim 7, wherein the first and second arch bars are bendable.

* * * * *